(12) United States Patent
Oshlack et al.

(10) Patent No.: US 6,645,527 B2
(45) Date of Patent: *Nov. 11, 2003

(54) STABILIZED SUSTAINED RELEASE TRAMADOL FORMULATIONS

(75) Inventors: Benjamin Oshlack, New York, NY (US); Hua-Pin Huang, Englewood Cliffs, NJ (US); Mark Chasin, Manalapan, NJ (US); Paul Goldenheim, Wilton, CT (US)

(73) Assignee: Euro-Celtique S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 10/052,844

(22) Filed: Oct. 19, 2001

(65) Prior Publication Data

US 2002/0102302 A1 Aug. 1, 2002

Related U.S. Application Data

(63) Continuation of application No. 09/109,615, filed on Jul. 2, 1998, now Pat. No. 6,306,438.
(60) Provisional application No. 60/051,602, filed on Jul. 2, 1997.

(51) Int. Cl.[7] ................................................. A61K 9/22
(52) U.S. Cl. ..................................................... 424/468
(58) Field of Search ................................ 424/468, 469, 424/470, 476, 484, 485, 486, 487, 488, 400

(56) References Cited

U.S. PATENT DOCUMENTS

| | | | |
|---|---|---|---|
| 3,870,790 A | 3/1975 | Lowey et al. | 424/19 |
| 3,901,968 A | 8/1975 | Cohen et al. | 424/22 |
| 3,901,969 A | 8/1975 | Cohen et al. | 424/22 |

(List continued on next page.)

FOREIGN PATENT DOCUMENTS

| | | | |
|---|---|---|---|
| AU | 653223 | 11/1992 | A61K/31/55 |
| EP | 0015381 A2 | 9/1980 | |
| EP | 0377517 | 1/1990 | |

(List continued on next page.)

OTHER PUBLICATIONS

J.B. Dressman, C. Jarvis, A.G. Ozturk, B.O. Palsson, and T.A. Wheatley, 18th Int. Symposium on Controlled Release of Bioactive Materials, p. 654–655, "Storage Effects on Release From Phenylpropanolamine HCl Pellets Coated with an Ethylcellulose–based Film," 1991, Amsterdam, Netherlands, Pub. By the Controlled Release Society, Inc.

D.L. Munday, A.R. Fassihi, 5th Congr. Int. Pharm. vol. 2, pp 55–60, Changes in Drug Release Rate, Effect of Temperature and Relative Humidity on Polymeric Film Coating, 1989, Assoc. Pharm. Galenique Ind., Chatenay Malabry, FR.

Derwent Abstract of JP 60166608 A.

*Primary Examiner*—Thurman K. Page
*Assistant Examiner*—Robert M. Joynes
(74) *Attorney, Agent, or Firm*—Davidson, Davidson & Kappel, LLC

(57) ABSTRACT

A stabilized sustained release oral solid dosage form which includes an effective amount of tramadol or a pharmaceutically acceptable salt thereof dispersed in a matrix of a hydrophobic material comprising a wax-like substance which was melted or softened during the preparation of the matrix, is cured at a temperature from about 35° C. to about 65° C. for a time period from about 4 to about 72 hours, such that the formulation, when subjected to in-vitro dissolution after exposure to accelerated storage conditions of at least one month at 40° C./75% RH, releases an amount of tramadol which does not vary at any given dissolution time point by more than about 20% of the total amount of tramadol released when compared to in-vitro dissolution conducted prior to subjecting the dosage form to the accelerated storage conditions.

43 Claims, 1 Drawing Sheet

U.S. PATENT DOCUMENTS

| | | | |
|---|---|---|---|
| 4,088,798 A | 5/1978 | Michaelis | 427/3 |
| 4,138,475 A | 2/1979 | McAinsh et al. | 424/19 |
| 4,548,990 A | 10/1985 | Mueller et al. | 525/123 |
| 4,600,645 A | 7/1986 | Ghebre-Sellassie et al. | 424/482 |
| 4,716,041 A | 12/1987 | Kjornaes et al. | 424/468 |
| 4,728,513 A | 3/1988 | Ventouras | 424/461 |
| 4,756,911 A | 7/1988 | Drost et al. | 424/468 |
| 4,766,012 A | 8/1988 | Valenti | 427/213.36 |
| 4,784,858 A | 11/1988 | Ventouras | 424/468 |
| 4,786,506 A | 11/1988 | Fontanelli | 424/470 |
| 4,795,327 A | 1/1989 | Gaylord et al. | 424/468 |
| 4,810,501 A | 3/1989 | Ghebre-Sellasie et al. | 424/469 |
| 4,837,004 A | 6/1989 | Wu et al. | 424/438 |
| 4,837,033 A | 6/1989 | Kokubo et al. | 424/494 |
| 4,849,229 A | 7/1989 | Gaylord et al. | 424/468 |
| 4,891,230 A | 1/1990 | Geoghegan et al. | 424/461 |
| 4,954,350 A | 9/1990 | Jones et al. | 424/493 |
| 5,008,118 A | 4/1991 | Iwanami | 424/498 |
| 5,009,897 A | 4/1991 | Brinker et al. | 424/469 |
| 5,019,397 A | 5/1991 | Wong et al. | 424/473 |
| 5,024,842 A | 6/1991 | Edgren et al. | 424/473 |
| 5,068,110 A | 11/1991 | Fawzi et al. | 424/462 |
| 5,077,053 A | 12/1991 | Kuncewitch et al. | 424/441 |
| 5,085,866 A | 2/1992 | Cowsar et al. | 424/481 |
| 5,096,717 A | 3/1992 | Wirth et al. | 424/490 |
| 5,112,621 A | 5/1992 | Stevens et al. | 424/497 |
| 5,122,384 A | 6/1992 | Paradissis et al. | 424/451 |
| 5,133,974 A | 7/1992 | Paradissis et al. | 424/472 |
| 5,158,777 A | 10/1992 | Abramowitz et al. | 424/458 |
| 5,160,742 A | 11/1992 | Mazer et al. | 424/469 |
| 5,178,866 A | 1/1993 | Wright et al. | 424/473 |
| 5,186,937 A | 2/1993 | Sparks et al. | 424/438 |
| 5,202,128 A | 4/1993 | Morella et al. | 424/469 |
| 5,202,159 A | 4/1993 | Chen et al. | 427/213.31 |
| 5,213,811 A | 5/1993 | Frisbee et al. | 424/493 |
| 5,219,621 A | 6/1993 | Geoghegan et al. | 424/462 |
| 5,273,760 A | 12/1993 | Oshlack et al. | 424/480 |
| 5,286,493 A | 2/1994 | Oshlack et al. | 424/468 |
| 5,288,505 A | 2/1994 | Deboeck et al. | 424/497 |
| 5,470,584 A | 11/1995 | Hendrickson et al. | 424/490 |
| 5,472,712 A | 12/1995 | Oshlack et al. | 424/480 |
| 5,580,578 A * | 12/1996 | Oshlack et al. | 424/468 |
| 5,591,452 A | 1/1997 | Miller et al. | 424/468 |
| 5,958,452 A | 9/1999 | Oshlack et al. | 424/457 |
| 5,965,161 A | 10/1999 | Oshlack et al. | 424/457 |
| 5,968,551 A * | 10/1999 | Oshlack et al. | 424/456 |
| 6,254,887 B1 | 7/2001 | Miller et al. | 424/468 |
| 6,306,438 B1 * | 10/2001 | Oshlack et al. | 424/468 |
| 6,326,027 B1 | 12/2001 | Miller et al. | 424/468 |
| 6,335,033 B2 | 1/2002 | Oshlack et al. | 424/457 |

FOREIGN PATENT DOCUMENTS

| | | | |
|---|---|---|---|
| EP | 0377518 | 1/1990 | |
| EP | 0514814 | 7/1990 | A61K/31/55 |
| EP | 0463877 | 6/1991 | |
| EP | 0441245 A1 | 8/1991 | |
| EP | 0624366 | 11/1994 | A61K/31/135 |
| EP | 0754465 A1 | 1/1997 | |
| GB | 2170104 | 7/1986 | |
| GB | 2178313 | 2/1987 | |
| JP | 55104211 | 8/1980 | |
| JP | 0166608 | 8/1985 | 424/472 |
| JP | 3232814 | 10/1991 | |
| JP | 753361 | 2/1995 | |
| WO | 9526753 | 12/1995 | |

* cited by examiner

STABILIZED SUSTAINED RELEASE TRAMADOL FORMULATIONS

This application is a continuation of U.S. application Ser. No. 09/109,615, filed Jul. 2, 1998, now U.S. Pat. No. 6,306,438, which claims the benefit of provisional application 60/051,602 filed Jul. 2, 1997.

BACKGROUND OF THE INVENTION

The present invention relates to sustained release matrix preparations containing tramadol or a pharmaceutically acceptable salt thereof as the therapeutically active agent.

Sustained release preparations are known to those skilled in the art to achieve a slow release of a drug over an extended period of time, thereby extending the duration of drug action over that achieved by conventional delivery. Preferably such a preparation maintains a drug concentration in the blood within the therapeutic range for 12 hours or more.

An important aspect of the manufacture, regulatory review and approval of all dosage forms concerns their stability over extended periods of time. The stability data obtained with regard to a particular dosage form directly affects its shelf-life. The stability of a pharmaceutical dosage form is related to maintaining its physical, chemical, microbiological, therapeutic, and toxicological properties when stored, i.e., in a particular container and environment. Stability study requirements are covered, e.g., in the Good Manufacturing Practices (GMPs), the U.S.P., as well as in the regulatory requirements of the country where approval to market a dosage form is being sought. In the United States, a request to test, and eventually market, a drug or a drug formulation may be made via a New Drug Application (NDA), an Abbreviated New Drug Application (ANDA) or an Investigational New Drug Applications (IND).

The agents used in sustained release dosage formulations often present special problems with regard to their physical stability during storage. For example, waxes which have been used in such formulations are known to undergo physical alterations on prolonged standing. Precautions may be taken to stabilize waxes at the time of manufacture or to prevent the change from occurring. Fats and waxy materials when used in purified states are known to crystallize in unstable forms, causing unpredictable variations in availability rates during stability testing at the time of manufacture and during later storage.

It is known that certain strategies can be undertaken to obtain stabilized controlled release formulations in many cases, such as insuring that the individual agents are in a stable form before they are incorporated into the product, and that processing does not change this condition, retarding the instability by including additional additives, and inducing the individual agents of the dosage form to reach a stable state before the product is finally completed.

It is also recognized that the moisture content of the product can also influence the stability of the product. Changes in the hydration level of a polymeric film, such as the ethyl celluloses, can alter the rate of water permeation and drug availability. Also, binders such as acacia are known to become less soluble when exposed to moisture and heat. However, moisture content of a product can be controlled fairly successfully by controls in the processing method and proper packaging of the product.

Hydrophobic polymers such as certain cellulose derivatives, zein, acrylic resins, waxes, higher aliphatic alcohols, and polylactic and polyglycolic acids have been used in the prior art to develop controlled release dosage forms. Methods of using these polymers to develop controlled release dosage forms such as tablets, capsules, suppositories, spheroids, beads or microspheres are to overcoat the individual dosage units with these hydrophobic polymers. It is known in the prior art that these hydrophobic coatings can be applied either from a solution, suspension or dry. Since most of these polymers have a low solubility in water, they are usually applied by dissolving the polymer in an organic solvent and spraying the solution onto the individual drug forms (such as beads or tablets) and evaporating off the solvent.

The use of organic solvents in the preparation of hydrophobic coatings is considered undesirable because of inherent problems with regard to flammability, carcinogenicity, environmental concerns, and safety in general. It considered very desirable in the art, however, to provide a controlled release coating derived from aqueous dispersions of a hydrophobic material. Unfortunately, such formulations were prone to changes in dissolution characteristics upon storage, rendering such formulations unsuitable for oral sustained release dosage forms containing therapeutically active agents. Stabilized controlled release formulations which utilize ethyl cellulose as a controlled release coating are described in the assignee's previous U.S. Pat. Nos. 5,273,760 and 5,472,712, hereby incorporated by reference. Stabilized controlled release formulations which utilize one or more acrylic polymers as a controlled release coating are described in the assignee's previous U.S. Pat. Nos. 5,286,493; 5,580,578; and 5,639,476, hereby incorporated by reference.

Sustained release oral dosage forms in which the therapeutically active agent is incorporated into a matrix containing one or more hydrophobic and/or hydrophilic materials are also well known to those skilled in the art. In this regard, reference is made to U.S. Pat. No. 3,965,256 (Leslie) which is directed to slow release pharmaceutical compositions comprising a combination of a higher aliphatic alcohol and a hydrated hydroxy-alkyl cellulose; and U.S. Pat. Nos. 4,861,598 and 4,970,075 (Oshlack, et al.), wherein the release of therapuetically active agents from controlled release bases is extended by using a combination of a higher aliphatic alcohol and an acrylic resin as the base material.

Melt granulation techniques have also been suggested to provide controlled release formulations. Melt granulation usually involves mechanically working an active ingredient in particulate form with one or more suitable binders and/or pharmaceutically acceptable excipients in a mixer until one or more of the binders melts and adheres to the surface of the particulate, eventually building up granules. This technique has been utilized in the exemplification of sustained release oral tramadol dosage formulations, as set forth in the assignee's U.S. Pat. No. 5,591,452, hereby incorporated by reference.

PCT International Publication No. WO 92/06679, incorporated by reference, discloses melt granulating methods for producing pellets containing therapeutically active substances. The method includes mechanically working a mixture containing the active substance in cohesive form with a binder having a melting point of 40–100° C., while supplying sufficient energy to melt the binder and form "overmoist" spherical pellets and thereafter adding an additional cohesive substance while maintaining the mechanical working to finally produce dry pellets.

PCT International Publication No. WO 93/18753, incorporated by reference, also discloses another melt extrusion process for preparing sustained release pellets. This method includes pelletizing a mixture containing drug in finely divided form and a binder which includes one or more water-insoluble-wax-like binder substances with a melting point above 40° C. using a high shear mixer.

OBJECTS AND SUMMARY OF THE INVENTION

It is an object of the present invention to provide an oral sustained release solid dosage form of tramadol suitable for at least twelve-hourly (e.g. up to twenty-four hourly) administration for the treatment of pain.

It is an object of the present invention to provide sustained release tramadol formulations which provide a stable dissolution, even after exposure to accelerated storage conditions or to prolonged storage at room temperature.

It is an object of the present invention to provide a method of preparing a sustained release tablet which includes tramadol as the drug which tablet provides a stable dissolution profile of the drug when plated in an environment of use, despite exposure to accelerated storage conditions.

A further object of the present invention is to provide a stabilized sustained release tramadol formulation wherein the sustained release is provided via a matrix of a hydrophobic material comprising a wax-like substance and the drug, wherein the wax-like substance is softened or melted during the preparation of the matrix, and which formulation provides a stable dissolution of an active agent contained in the formulation, despite exposure to accelerated storage conditions such that the dissolution would be deemed acceptable by a governmental regulatory agency such as the U.S. Food and Drug Administration ("FDA") for purposes of according expiration dating.

It is another object of the present invention to provide a method of preparing a sustained release tramadol tablet containing a hydrophobic material which comprises a wax-like substance such that there is a stable dissolution profile of the tramadol when placed in an environment of use, despite exposure to accelerated storage conditions.

These objects and others have been accomplished by the present invention, which relates in part to a stabilized sustained release oral solid dosage form or formulation containing tramadol or a pharmaceutically acceptable salt or complex thereof in a matrix comprising a hydrophobic material which has been softened or melted during the preparation of the dosage form, which dosage form after preparation of the matrix containing the tramadol is cured at a suitable temperature (e.g., a temperature above the glass transition temperature of the hydrophobic material (in the case of polymers) until an endpoint is reached at which the cured dosage form, when subjected to in-vitro dissolution, releases the tramadol in amounts which do not vary at any time point along the dissolution curve by more than about 20% of the total amount of tramadol released, when compared to the in-vitro dissolution of the formulation prior to curing.

The invention is further directed to a stabilized sustained release oral solid dosage form containing tramadol as the active agent, comprising an effective amount of tramadol or a pharmaceutically acceptable salt thereof dispersed in a matrix of a hydrophobic material comprising a wax-like substance which was melted or softened during the preparation of said matrix. The solid dosage form is cured at a sufficient temperature and for a sufficient time such that an endpoint is reached at which said solid dosage form provides a stable dissolution profile. The endpoint is determined by comparing the dissolution profile of said solid dosage form immediately after curing to the dissolution profile of said solid dosage form after exposure to accelerated storage conditions of at least one month at 40° C. and 75% relative humidity. The curing is preferably conducted at a temperature from about 35° C. to about 65° C., preferably from about 40° C. to about 60° C., preferably for a time period from about 4 to about 72 hours. In certain preferred embodiments, the curing is preferably conducted for a time period of about 24 hours or more, until the endpoint is reached. In certain embodiments, the curing is conducted at a temperature from about 45° C. to about 55° C. for a time period from about 4 to about 72 hours, preferably for a time period of about 24 hours, until the endpoint is reached. The wax-like substance may be selected from the group consisting of hydrogenated vegetable oil, hydrogenated castor oil, paraffin, higher aliphatic alcohols, higher aliphatic acids, long chain fatty acids, fatty acid esters, and mixtures thereof. The hydrophobic material may further comprise a hydrophobic polymer—selected from the group consisting of acrylic polymers, alkylcelluloses and mixtures thereof. Further, the matrix may contain a hydrophilic polymer, e.g., a cellulose ether, or other hydrophilic material. The sustained release dosage form may be in the form of a unit dose of multiparticulates, or a tablet.

In certain preferred embodiments, the matrix of the stabilized sustained release oral solid dosage form comprises tramadol, a higher aliphatic alcohol, and a hydrophobic polymer selected from the group consisting of acrylic polymers, alkylcelluloses and mixtures thereof. In other preferred embodiments, the matrix of the stabilized sustained release oral solid dosage form comprises tramadol and hydrogenated vegetable oil.

Another aspect of the invention provides a method of preparing a sustained release oral solid dosage form containing tramadol as the active ingredient. This method includes mixing tramadol together with a hydrophobic material and an optional binder to form a homogeneous mixture, heating the mixture and thereafter extruding and granulating the mixture. Thereafter the granulate is preferably compressed into tablets (after mixing with optional pharmaceutical excipients such as talc and a lubricant such as magnesium stearate), and the tablets cured as described herein. In alternative embodiments, the granulate (or the extrudate cut into appropriately sized particles) is cured as described herein and then the granulate is divided into suitable unit dosages of tramadol (e.g., filled into pharmaceutically acceptable gelatin capsules). In preferred embodiments, the curing is conducted at a temperature from about 35° C. to about 65° C., preferably about 40° C. to about 60° C., for a time period from about 4 to about 72 hours, preferably at least about 24 hours. In further preferred embodiments, the curing is conducted at a temperature from about 45° C. to about 55° C. for a time period from about 4 to about 72 hours, preferably at least about 24 hours.

The invention further relates to a process for preparing a stabilized sustained release oral solid dosage form containing tramadol as the active agent, comprising preparing a matrix comprising tramadol or a pharmaceutically acceptable salt thereof dispersed in a matrix of a hydrophobic material comprising a wax-like substance, wherein the wax-like substance is melted or softened during the preparation of said matrix; and thereafter curing the matrix at a sufficient temperature and for a sufficient time such that an endpoint is reached at which the matrix provides a stable dissolution profile. The endpoint is determined by comparing the dissolution profile of the matrix immediately after curing to the dissolution profile of the matrix after exposure to accelerated storage conditions of at least one month at 40° C. and 75% relative humidity. The matrix may comprise a plurality of pharmaceutically acceptable particles (such as granules), or the matrix may comprise a tablet. In preferred embodiments, the matrix is compressed into a tablet. The process for preparing a stabilized sustained release oral solid dosage form containing tramadol in accordance with the present invention may be any process which includes a wax or wax-like material in the matrix, and where the wax or wax-like material is softened or melted during preparation of the dosage form. In certain preferred embodiments, the formulation is prepared by feeding tramadol and hydrophobic material, together with further optional pharmaceutical excipients, into an extruder at elevated temperatures sufficient to soften or melt the wax-like material; extruding the mixture; granulating the mixture; lubricating the granulate; and then optionally compressing the granulate into tablets. In other preferred embodiments, the formulations are prepared by spraying a hydrophobic polymer dispersion onto a mixture of tramadol and an inert diluent in a fluid bed dryer to obtain granulates; mixing molten wax-like substance into the granulates in a high shear mixer; passing the mixture through a screen and mixing with talc; lubricating the resultant material; and optionally compressing the lubricated granulates into tablets. In yet further preferred embodiments of the invention, the formulation is prepared by pouring molten wax-like substance onto the tramadol in a pharmaceutically suitable mixer; allowing the mixture to congeal and cool; and thereafter milling the mixture; lubricating the mixture; and compressing the lubricated granulation into tablets. In a further alternative preferred method, the formulations of the invention are prepared by melting and granulating a wax-like substance; hydrating a cellulose ether and granulating the same; blending the tramadol with either the granulated melt, the granulated cellulose ether, or a mixture thereof; drying the granules; and thereafter optionally mixing with an appropriate amount of a inert pharmaceutically acceptable diluent and compressing the mixture tablets.

In embodiments where the hydrophobic material comprises a hydrophilic or hydrophobic polymer in addition to the wax-like substance, the formulation may be prepared by (a) wet granulating the hydrophobic or hydrophilic polymer and optional diluents with or without the tramadol; (b) drying and sizing the resultant granulate; (c) combining said tramadol with the granulate if not previously accomplished in step (a); incorporating the wax-like substance in a molten state into the granules using a suitable mixer; (d) cooling and sizing the granules; and thereafter (e) optionally lubricating the granules compressing the lubricated granules into tablets.

In yet a further aspect of the invention, there is provided a method of treating a patient by administering the sustained release oral solid dosage forms of tramadol which provide a stable dissolution as described herein.

In preferred embodiments of the invention, the curing of the solid dosage form containing tramadol gradually slows the release of said active agent when exposed to an environmental fluid, such that the cured formulation provides a stabilized dissolution of tramadol which is unchanged after exposure to accelerated storage conditions, the stabilized dissolution being deemed appropriate by the United States Food & Drug Administration, the Committee on Proprietary Medicinal Products ("CPMP") in Europe, and other similar Governmental Regulatory Authorities, for the purpose of according expiration dating for said formulation. The curing may continue, for example, for a sufficient period of time until a curing endpoint is reached to provide a stabilized dissolution of tramadol from the dosage form which is unchanged after exposure to accelerated storage conditions. The endpoint may be determined by comparing the dissolution profile of the formulation immediately after curing to the dissolution profile of the formulation after exposure to accelerated storage conditions, e.g., of one-three months at a temperature of 37° C. and at a relative humidity of 80%.

In other preferred embodiments, the curing of the sustained release oral solid dosage form, after exposure to accelerated storage conditions of at least one month at 40° C./75% RH, releases an amount of tramadol which does not vary at any given dissolution time point by more than about 20% of the total amount of tramadol released, when compared to in-vitro dissolution conducted prior to storage.

In other embodiments, the oral sustained release solid dosage form of tramadol, upon in-vitro dissolution testing, provides a band range after exposure to accelerated storage conditions which is not wider than about 20% at any point of time when compared to the dissolution profile prior to exposure to the accelerated storage conditions.

The terms "stable dissolution profile" and "curing endpoint" are defined for purposes of the present invention as meaning that the cured solid dosage form (e.g., tablet) reproducibly provides a release of the active agent (e.g., tramadol) when placed in an environment of use which is unchanged, even after exposing the cured formulation to accelerated storage conditions. Those skilled in the art will recognize that by "unchanged" it is meant that any change in the release of the active agent from the cured formulation would be deemed insignificant in terms of the desired effect. For pharmaceutical formulations, stability is determined by, e.g., a regulatory agency such as the Food & Drug Administration (FDA) in the U.S., or the Committee on Proprietary Medicinal Products ("CPMP") in Europe, for the purpose of according an expiration date for the formulation.

By the phrase "accelerated storage conditions" it is meant, e.g., storage conditions of elevated temperature and/or elevated relative humidity. Preferably, the phrase "accelerated storage conditions" refers to storage conditions to which the final drug formulation is subjected for the purpose of obtaining regulatory approval (e.g., FDA approval in the U.S.) and an expiration date.

The term "expiration date" is defined for purposes of the present invention as the date designating the time during which a batch of the product (e.g., the cured, coated substrate) is expected to remain within specification if stored under defined conditions, and after which it should not be used.

The term "band range" for purposes of the present invention is defined as the difference in in-vitro dissolution measurements of the controlled release formulations when comparing the dissolution profile (curve) obtained by the formulation upon completion of the manufacturing of the coated product (prior to storage) and the dissolution profile obtained after the coated product is exposed to accelerated storage conditions, expressed as the change in percent of the active agent released from the coated product at any dissolution time point along the dissolution curves.

The term "sustained release" is defined for purposes of the present invention as the release of the drug (i.e., tramadol) at such a rate that blood (e.g., plasma) levels are maintained within the therapeutic range but below toxic levels over a period of time greater than 6 hours, more preferably for periods of about 12 hours (i.e., twice-a-day) or about 24 hours (i.e., once-a-day), or longer. The term sustained release is deemed to encompass the term "prolonged release" as that term is used by the CPMP.

The term "curing" is defined for purposes of the present invention as the heat treatment of the dosage form (or intermediate product) for purposes of obtaining a stabilized final oral pharmaceutical sustained release dosage form as defined above. When the formulations of the invention incorporate a polymer as part or all of the hydrophobic retarding agent, it will be appreciated by those skilled in the art that a heat treatment causes a curing effect and that the polymer possibly cross-links with itself into a more stable state. When the formulations of the invention do not incorporate a polymer but rather include a hydrophobic material such as, e.g., hydrogenated vegetable oil or stearyl alcohol, one skilled in the art will appreciate that the heat treatment is more akin to an annealing of the formulation rather than a curing of the polymer. However, for purposes of the present invention, the use of the term "curing" is deemed to encompass both curing and/or annealing.

BRIEF DESCRIPTION OF THE DRAWINGS

The following drawings are illustrative of embodiments of the invention and are not meant to limit the scope of the invention as encompassed by the claims.

DETAILED DESCRIPTION

Figure 1:
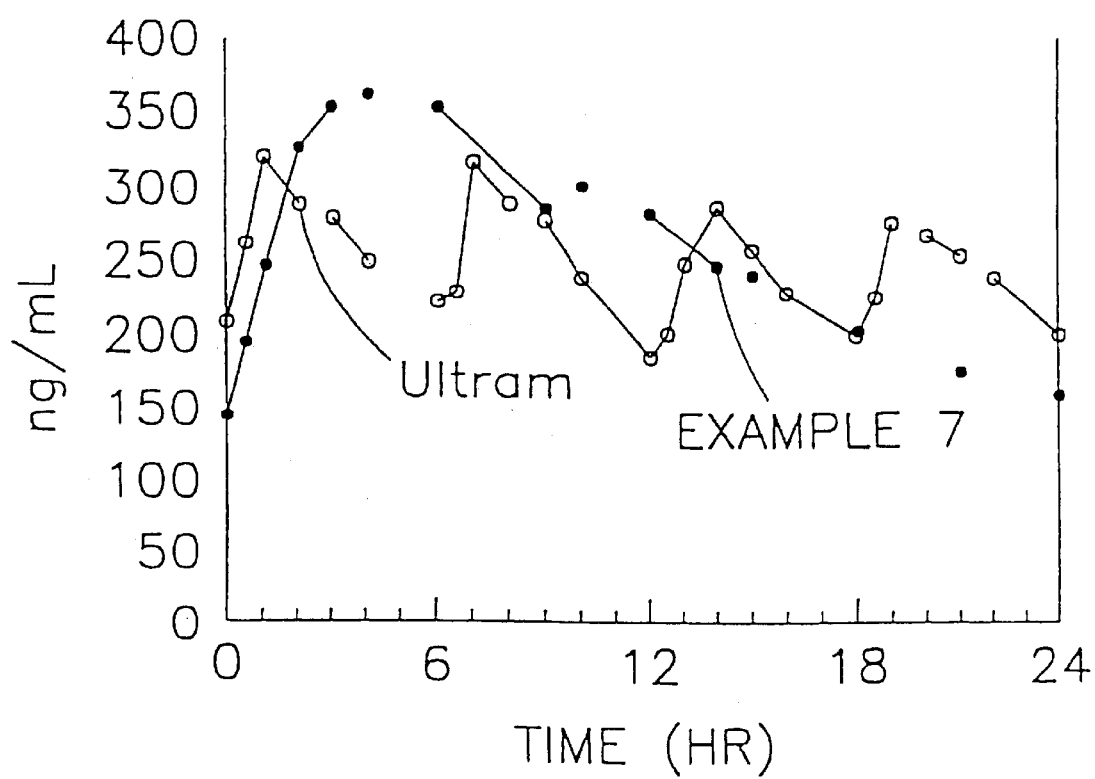
FIG. 1 is a graphical representation of the mean plasma tramadol concentrations (ng/ml) over 24 hours on the fifth day after multiple doses of Example 7 and Ultram™.

Tramadol, which has the chemical name (±)-trans-2-[(dimethylamino)methyl]-1-(3-methoxyphenyl)cyclohexanol, is an orally active opioid analgesic. Conventional release preparations in the form of capsules, drops and suppositories containing tramadol, or more particularly its hydrochloride salt, have been commercially available for many years for use in the treatment of moderate to severe pain. Such preparations, however, do not provide a sustained release of the tramadol. Moreover, despite long-standing use of tramadol, sustained release preparations for oral administration containing tramadol as active ingredient have not even previously been described in the literature.

Suitable pharmaceutically acceptable salts of tramadol for use according to the present invention are those conventionally known in the art such as pharmaceutically acceptable acid addition salts. The hydrochloride salt is particularly preferred.

According to the present invention, in order to obtain a controlled release of the active agent, the therapeutically active agent is homogeneously combined with a sufficient amount of a hydrophobic (release-retardant) material which comprises a wax or a wax-like material. The hydrophobic material may also include a hydrophobic polymer, e.g., a water-insoluble acrylic polymer or alkylcellulose.

It has been surprisingly discovered that when a sustained release matrix formulation of tramadol is prepared in which the wax or wax-like material is incorporated by means of a process in which it is softened or melted, the final sustained release matrix formulation (e.g., tablet) does not provide a stable dissolution profile after exposure to accelerated storage conditions, as these terms are defined herein. It is hypothesized that tramadol itself has physical characteristics which make such formulations "softer". In other words, it is hypothesized that tramadol itself has a plasticizing effect on such matrix formulations which include a softened or melted wax or wax-like material, and that this physical property of tramadol contributes to the lack of stability in such products. It should be recognized that these hypotheses are provided for explanation purposes only; the inventors do not intend to be limited by such hypotheses and the appended claims should not be interpreted in such a manner.

By virtue of the present invention, however, sustained release matrix formulations containing tramadol within a matrix which includes a wax or a wax-like material can now be prepared in a manner that provides stability to the formulation (as stability is defined herein).

More particularly, in the present invention, the final product, such as a tablet, is cured to an endpoint at which the tablet provides a reproducible stable dissolution profile, even after exposure to accelerated storage conditions or after prolonged storage at room temperature.

Pharmaceutical dosage forms may be developed in which the rate of release of active substance(s) has in some way been modified compared with conventional formulations. Such modification in release of active substances may have a number of objectives but the intention of this note for guidance is to cover those formulations in which the release of the active substance is prolonged in some way in order to maintain therapeutic activity to reduce toxic effects or for some other therapeutic purpose.

As set forth in the "Notes for Guidance on Prolonged Release Oral Dosage Forms", Form 3A115A (January 1996) from the European Committee on Proprietary Medicinal Products ("CPMP"), the details required in the application for marketing authorization generally will reflect: the therapeutic intention; the nature of the active substance; the nature of the formulation, the route of administration, and data must be provided in the various sections of the dossier in support of the application taking into account these various requirements. Areas which need to be addressed in the application for marketing authorization include in-vitro testing of oral solid dosage forms in which release of active substance forms the rate-limiting step in absorption.

The afore-mentioned CPMP guidline indicates that the release rate should be tested in-vitro by a dissolution test method which has been shown to discriminate between batches with acceptable and unacceptable in-vivo performance. Test conditions providing the most suitable discrimination should be chosen. The dissolution apparatus should preferably be one of those accepted by the agency reviewing the application. For example, in Europe, the dissolution apparatus is preferably described in the U.S. or European Pharmacopoeia. In such test methods, the test medium should preferably be aqueous-based; organic or aqueous-organic media are preferably avoided. For poorly soluble substances, a minimal content of an appropriate surfactant may be added. Buffer solutions at a number of pH values spanning the physiological rate (pH 0.8–2, stomach; pH 5–6.5, jejunum; pH 6–7.5, ileum; Davis et al 1989) may be used to determine the relationship between dissolution and pH. The data obtained could usefully be represented using three-dimensional dissolution profiles (i.e. % dissolved as a function of time and pH).

In order to achieve adequate discrimination, the CPMP Guidline indicates that it may be necessary to limit the solubility of the medicinal product (therapeutically active agent) and still achieve sink conditions in the dissolution medium. It may also be necessary to consider the ionic strength and surface tension of the medium. The volume of medium used should preferably ensure sink conditions which may be assumed if the amount of substance in solution does not exceed 30% of the saturation concentration. The solubility of the substance in the chosen dissolution medium should be stated. Identical test conditions should be used for different strengths of the same product. The robustness of the dissolution test should be determined by examining the effect on the dissolution rate of variations in temperature, pH and speed of rotation.

The definitive dissolution profile and the corresponding specification (for marketing authorization) is preferably based on in-vitro results of batches used in in-vivo testing and preferably provides an assurance that batches will routinely give the desired in-vivo behavior.

To justify the specification limits of the in-vitro dissolution test, the CPMP Guidline indicates that an attempt be made to establish a meaningful correlation between in-vitro release characteristics and in-vivo bioavailability parameters. In order to accomplish this, a number of techniques may be employed. These include, in order of decreasing predictive power:

a) comparison of the in-vitro dissolution curve of the product with the in-vivo dissolution curves generated by deconvolution of plasma level data or by other appropriate methods;

b) comparison of the mean in-vitro dissolution time of the product to either the mean in-vivo residence time or the mean in-vivo dissolution time of the product derived by using the principles of statistical moment analysis;

c) comparison of the mean in-vitro dissolution time to one mean pharmacokinetic parameter, e.g., time to maximum plasma concentration ("Tmax").

Other approaches are considered acceptable, especially if the above methods fail to demonstrate a correlation. Examples of other approaches include demonstrating bioequivalence of the proposed formulation to formulations with dissolution profiles at the upper and lower limits of the specification, or alternatively, the specification limits may be derived from the spread of in-vitro dissolution results of batches used in bioavailability testing. The regulatory authorities generally desire that the choice of approach should be justified by the applicant for marketing authorization.

The finished product specification in an application for marketing authorization generally includes a dissolution test. The dissolution specification is of importance not only to ensure consistent substance release from batch to batch at time of manufacture but also to set acceptance limits for the dissolution of the product during its shelf life. The dissolution specification should be deduced from the profile(s) obtained during the development of the product and revalidated with at least pilot production scale batches. Selection of specifications should take into account pharmacokinetics, pharmacodynamics and in-vitro assay precision. Generally (and specifically with respect to the afore-mentioned CPMP Guidline), a minimum of three points should be included: an early time point to exclude dose dumping, at least one point to ensure compliance with the shape of the dissolution profile and one to ensure that the majority of the substance has been released. Where both upper and lower limits are specified at any time point, the difference between them should not usually exceed 20% of the labelled content of active substance in the formulation unless wider limits have been shown to provide reproducible and acceptable in-vivo performance.

Regulations of the appropriate agency, e.g., the U.S. FDA or the CPMP, require demonstration that the dissolution profile of the active substance is maintained within specification throughout the proposed shelf life of the product.

Where the dissolution specification has been correlated with in-vivo results, minor changes to the data may be acceptable on the basis of in-vitro testing. Minor changes include changes to the composition (e.g. nature and/or quantity of excipients which do not influence the release characteristics) method or site of manufacture or manufacturing equipment. Other changes may however necessitate further in-vitro/in-vivo correlation studies or in-vivo bioavailability studies.

Hydrophobic Material

The hydrophobic material comprises a wax or wax-like material (hereinafter referred to as "wax-like substance"). The hydrophobic material used in the formulations of the present invention is a material such as a natural or synthetic wax or oil, for example hydrogenated fats such as hydrogenated vegetable oil, hydrogenated castor oil, microcrystalline wax, normal waxes, beeswax, carnauba wax, paraffin, or glyceryl monostearate, and suitably has a melting point of from 35 to 140° C., preferably 45 to 110° C. Hydrogenated vegetable oil is especially preferred. Alternatively or in addition to the above materials, the wax or wax-like substance used in the formulations of the present invention may comprise fatty alcohols, fatty acid esters, fatty acid glycerides (mono-, di-, and tri-glycerides), higher aliphatic (e.g., $C_{10}$–$C_{20}$) acids, alcohols, long chain fatty acids, and mixtures thereof. Useful water-insoluble wax-like substances may be those with a water-solubility that is lower than about 1:5,000 (w/w).

The aliphatic alcohol may conveniently be lauryl alcohol, myristyl alcohol or stearyl alcohol but is preferably cetyl alcohol or more preferably cetostearyl alcohol.

In addition to the wax-like substance, certain preferred embodiments include a further hydrophobic polymer as part of the hydrophobic material.

One particularly suitable sustained release matrix includes a hydrophobic polymer which comprises one or more alkylcelluloses and one or more $C_{12}$–$C_{36}$ aliphatic alcohols. The alkylcellulose is preferably $C_1$–$C_6$ alkyl cellulose, especially ethylcellulose.

In other embodiments of the present invention, the hydrophobic polymer is a pharmaceutically acceptable acrylic polymer, including but not limited to acrylic acid and methacrylic acid copolymers, methyl methacrylate copolymers, ethoxyethyl methacrylates, cynaoethyl methacrylate, aminoalkyl methacrylate copolymer, poly (acrylic acid), poly(methacrylic acid), methacrylic acid alkylamide copolymer, poly(methyl methacrylate), poly (methacrylic acid) (anhydride), methyl methacrylate, polymethacrylate, poly(methyl methacrylate), poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups. Such an acrylic polymer is an acrylic resin lacquer commercially available from Rohm Pharma under the Tradename Eudragit®.

Other hydrophobic polymers which may be used in the formulations of the present invention include cellulosic polymers, including other alkyl cellulosic polymers such as ethylcellulose.

The release of the active agent from the controlled release formulation of the present invention can be further influenced, i.e., adjusted to a desired rate, by the addition of one or more release-modifying agents into the matrix. The release-modifying agents may comprise one or more water-soluble hydrophilic polymers in order to modify the release characteristics of the formulation. Examples of suitable hydrophilic polymers include hydroxypropylmethylcellulose, cellulose ethers, acrylic resins and protein-derived materials. Of these polymers, the cellulose ethers, especially hydroxyalkylcelluloses and carboxyalkylcelluloses, are preferred. Also, synthetic water-soluble polymers may be used, such as polyvinylpyrrolidone, cross-linked polyvinylpyrrolidone, polyethylene oxide, etc., and polysaccharides, e.g., pullulan, dextran, sucrose, glucose, fructose, mannitol, lactose, mannose, galactose, sorbitol and mixtures thereof. In certain preferred embodiments of the present invention, the hydrophilic polymer comprises hydroxypropylmethylcellulose.

Semipermeable polymers may also be incorporated in the matrix to change the release characteristics of the formulation. Such semipermeable polymers include, for example, cellulose acylates, acetates, and other semipermeable polymers such as those described in U.S. Pat. No. 4,285,987 (hereby incorporated by reference), as well as the selectively permeable polymers formed by the coprecipitation of a polycation and a polyanion as disclosed in U.S. Pat. Nos. 3,173,876; 3,276,586; 3,541,005; 3,541,006 and 3,546,142 (hereby incorporated by reference).

The hydrophobic polymers typically require a plasticizer. Examples of suitable plasticizers for ethylcellulose include water insoluble plasticizers such as dibutyl citrate, dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Examples of suitable plasticizers for the acrylic polymers of the present invention include citric acid esters such as triethyl citrate NF XVI, tributyl citrate, dibutyl phthalate, and possibly 1,2-propylene glycol, polyethylene glycols, propylene glycol, diethyl phthalate, castor oil, and triacetin, although it is possible that other water-insoluble plasticizers (such as acetylated monoglycerides, phthalate esters, castor oil, etc.) may be used.

Surprisingly however, embodiments of the present invention can be prepared without the presence of a plasticizer. Such embodiments are typically prepared via the melt extrusion processes described herein, and are not expected in view of the prior art.

In addition to the foregoing, the sustained release formulations of the invention may include pharmaceutically acceptable carriers and excipients. It is to be understood that these materials, for example, can be mixed with the particles after extrusion as well. Specific examples of pharmaceutically acceptable carriers and excipients that may be used to formulate oral dosage forms are described in the *Handbook of Pharmaceutical Excipients,* American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) Second Edition, published by Marcel Dekker, Inc., incorporated by reference herein. Techniques and compositions for making tablets (compressed and molded), capsules (hard and soft gelatin) and pills are also described in *Remington's Pharmaceutical Sciences,* (Arthur Osol, editor), 1553–1593 (1980), incorporated by reference herein. Pharmaceutically acceptable ingredients which are conventional in the pharmaceutical art include diluents, lubricants, binders, granulating aids, colorants, flavorants, surfactants, pH adjusters, anti-adherents and glidants, e.g. dibutyl sebacate, ammonium hydroxide, oleic acid and colloidal silica.

The sustained release preparation according to the invention may be presented, for example, as granules, multiparticulates, capsules, or tablets. Tablets are preferred. The sustained release formulations according to the invention may conveniently be film coated using any film coating material conventional in the pharmaceutical art. Preferably an aqueous film coating is used.

In certain embodiments of the invention, the granules or tablets are film-coated. The granules may be film-coated and then either divided into unit doses of tramadol (e.g., and placed in a gelatin capsule), or compressed into a tablet. Likewise, the tablets prepared in accordance with the invention may be film-coated. The film coated may be accomplished prior to or after the curing step. Generally, the film-coating substantially comprises a hydrophilic polymer such as hydroxypropylmethylcellulose and does not affect the rate of release of the drug from the formulation. The film-coatings which may be used preferably are capable of producing a strong, continuous film that is smooth and elegant, capable of supporting pigments and other coating additives, non-toxic, inert, and tack-free.

In certain further embodiments of the invention, the film-coating may contribute to the release properties of the dosage form. In such cases, the dosage form, e.g. granules or tablets, may be coated with a sufficient amount of hydrophobic material to obtain a weight gain level from about 1 to about 30 percent. The solvent which is used for the hydrophobic material may be any pharmaceutically acceptable solvent, including water, methanol, ethanol, methylene chloride and mixtures thereof. It is preferable however, that the coatings be based upon aqueous dispersions of the hydrophobic material. The hydrophobic polymer used in such film-coatings may comprise, for example, a pharmaceutically acceptable acrylic polymer, including but not limited to acrylic acid and methacrylic acid copolymers, or an alkylcellulose such as ethylcellulose, such as a commercially-available aqueous dispersion of ethylcellulose known as Aquacoat® (FMC Corp., Philadelphia, Pa., U.S.A.). The acrylic polymer in certain instances is preferably one or more ammonio methacrylate copolymers commercially available from Rohm Pharma under the Tradename Eudragit®. To produce tablets in accordance with the invention, particles produced in accordance with the invention may be mixed or blended with the desired excipient(s), if any, using conventional procedures, e.g. using a Y-Cone or bin-blender and the resulting mixture compressed according to conventional tableting procedure using a suitable size tableting mold. Tablets can be produced using conventional tableting machines, and in the embodiments described below were produced on standard single punch F3 Manesty machine or Kilian RLE15 rotary tablet machine. The tablets of the present invention may be any suitable shape, such as round, oval, biconcave, hemispherical, any polygonal shape such as square, rectangular, and pentagonal, and the like.

The active ingredient (tramadol) in the formulations according to the present invention is incorporated into a controlled release matrix. The matrix preferably affords sustained release tramadol over at least a twelve hour period and preferably that affords in-vitro dissolution rates and in-vivo absorption rates of tramadol within the ranges specified herein. The total amount of tramadol or pharmaceutically acceptable salt thereof in the matrices of the invention may vary within wide limits, for example from about 20 to about 80%, preferably from about 40 to about 60%, and most preferably from about 45 to about 55%, by weight. The total amount of hydrophobic material in the matrices of the invention may be from about 80 to about 20%, by weight. The total portion of hydrophobic polymer (not a wax-like substance as defined herein) as a component of the hydrophobic material may be from about 0 to about 80%, in certain preferred embodiments is preferably from about 20 to about 60%, and most preferably from about 30 to about 50%, by weight. The total amount of additional optional pharmaceutically acceptable ingredients, including inert diluent(s), lubricants, etc. may be from about 0 (preferably 0.5%) to about 10% of the total weight of the formulation.

In an especially preferred embodiment, the sustained release matrix includes a hydrophobic polymer (e.g., ethyl cellulose) and a higher aliphatic alcohol (e.g., cetostearyl alcohol), with or without an optional plasticizer.

In order to allow for sustained release tramadol over at least a twelve hour period following oral administration, the in-vitro release rate preferably corresponds to the following % rate of tramadol released: from about 1 to about 50% tramadol released after 1 hour; from about 0 to about 75% tramadol released after about 2 hours; from about 3 to about 95% tramadol released after about 4 hours; from about 10 to about 100% tramadol released after about 8 hours; from about 20 to about 100% tramadol released after about 12 hours; from about 30 to about 100% tramadol released after about 16 hours; from about 50 to about 100% tramadol released after about 24 hours; and more than 80% tramadol released after about 36 hours.

Another preferred preparation especially suited for twice-a-day dosing has an in-vitro release rate corresponding to the following percentage (%) rate of tramadol released: from about 20 to about 50% tramadol released after about 1 hour; from about 40 to about 75% tramadol released after about 2 hours; from about 60 to about 95% tramadol released after about 4 hours; from about 80 to about 100% tramadol released after about 8 hours; and from about 90 to about 100% tramadol released after about 12 hours.

Yet another preferred particularly suited for once-a-day dosing has an in-vitro release rate corresponding to the following % rate of tramadol released: from about 0 to about 50% tramadol released after about 1 hour; from about 0 to about 75% tramadol released after about 2 hours; from about 10 to about 95% tramadol released after about 4 hours; from about 35 to about 100% tramadol released after about 8 hours; from about 55 to about 100% tramadol released after about 12 hours; from about 70 to about 100% tramadol released after about 16 hours; and more than about 90% tramadol released after about 24 hours.

A still further preferred preparation in accordance with the invention also particularly suited for once-a-day dosing has an in-vitro release rate corresponding to the following % rate of tramadol released: from about 0 to about 30% tramadol released after about 1 hour; from about 0 to about 40% tramadol released after 2 hours; from about 3 to about 55% tramadol released after about 4 hours; from about 10 to about 65% tramadol released after about 8 hours; from about 20 to about 75% tramadol released after about 12 hours; from about 30 to about 88% tramadol released after about 16 hours; from about 50 to about 100% tramadol released after about 24 hours; and more than about 80% tramadol released after about 36 hours. More preferably a preparation of once-a-day dosing as an in-vitro release rate substantially as follows: from about 15 to about 25% tramadol released after about 1 hour; from about 25 to about 35% tramadol released after about 2 hours; from about 30 to about 45% tramadol released after about 4 hours; from about 40 to about 60% tramadol released after about 8 hours; from about 55 to about 70% tramadol released after about 12 hours; and from about 60 to about 75% tramadol released after about 16 hours.

Another preferred dissolution rate in-vitro upon release of the sustained release preparation for administration twice daily according to the invention, is between about 5 and about 50% (by weight) tramadol released after about 1 hour, between about 10 and about 75% (by weight) tramadol released after about 2 hours, between about 20 and about 95% (by weight) tramadol released after about 4 hours, between about 40 and about 100% (by weight) tramadol released after about 8 hours, more than about 50% (by weight) tramadol released after about 12 hours, more than about 70% (by weight) tramadol released after about 18 hours and more than about 80% (by weight) tramadol released after about 24 hours.

Furthermore, it is preferred in the case of a sustained release preparation for administration twice daily that after about 8 hours following oral administration between about 70 and about 95% (by weight) tramadol is absorbed in-vivo, between about 77 and about 97% (by weight) tramadol is absorbed after about 10 hours and between about 80 and about 100% (by weight) tramadol is absorbed after about 12 hours.

A formulation in accordance with the invention suitable for twice-a-day dosing may have a $T_{max}$ from about 1.5 to about 8 hours, preferably from about 2 to about 7 hours, and a $W_{50}$ value in the range from about 7 to about 16 hours.

A formulation in accordance with the invention suitable for once-a-day dosing may have a $T_{max}$ in the range of about 3 to about 6 hours, preferably about 4 to about 5 hours and a $W_{50}$ value in the range about 10 to about 33 hours.

The $W_{50}$ parameter defines the width of the plasma profile at 50% $C_{max}$, i.e. the duration over which the plasma concentrations are equal to or greater than 50% of the peak concentration. The parameter is determined by linear interpolation of the observed data and represents the difference in time between the first (or only) upslope crossing and the last (or only) downslope crossing in the plasma profile.

The in-vitro release rates mentioned herein are, except where otherwise specified, those obtained by measurement using the USP Apparatus 2 (Paddle Method) at 100 rpm in pH 6.5 phosphate buffer at 37° C. The in-vivo absorption rate may be determined from measurement of plasma concentration against time using the deconvolution technique, or via an HPLC method.

The sustained release formulation according to the invention preferably contains an analgesically effective amount of tramadol or a pharmaceutically acceptable salt thereof, conveniently in the range of from about 50 to about 800 mg, especially 100, 200, 300, 400 or 600 mg (calculated as tramadol hydrochloride) per dosage unit.

The sustained release formulations of the present invention slowly release the therapeutically active agent, e.g., when ingested and exposed to gastric fluids, and then to intestinal fluids. The sustained release profile of the formulations of the invention can be altered, for example, by varying the amount of retardant, i.e., hydrophobic polymer, by varying the amount of plasticizer relative to hydrophobic polymer, by the inclusion of additional ingredients or excipients, by altering the method of manufacture, etc.

Preparation of the Dosage Forms

The formulations of the invention may be manufactured according to any of a multitude of processes known to those skilled in the art of pharmaceutical formulation where the hydrophobic material incorporated into the matrix is at least softened or melted.

One especially preferred process for preparing the dosage forms of the present invention (both multiparticulates and tablets) includes directly metering into an extruder a water-insoluble retardant, a therapeutically active agent, and an optional binder; heating said homogenous mixture; extruding said homogenous mixture to thereby form strands; cooling said strands containing said homogeneous mixture; and cutting said strands into particles having a size from about 0.1 mm to about 12 mm; and dividing said particles into unit doses. In this aspect of the invention, a relatively continuous manufacturing procedure is realized.

In a preferred embodiment, oral dosage forms are prepared to include an effective amount of multiparticulates by granulating the extrudate, and thereafter compressing the lubricated granulate into tablets. Alternatively, a plurality of the melt extruded particles may be placed in a gelatin capsule.

A typical melt extrusion system capable of carrying-out the present invention include a suitable extruder drive motor having variable speed and constant torque control, start-stop controls, and ammeter. In addition, the system will include a temperature control console which includes temperature sensors, cooling means and temperature indicators throughout the length of the extruder. In addition, the system will include an extruder such as a twin-screw extruder which consists of two counter-rotating intermeshing screws enclosed within a cyclinder or barrel having an aperture or die at the exit thereof. The feed materials enter through a feed hopper and is moved through the barrel by the screws and forced through the die into strands which are thereafter conveyed such as by a continuous movable belt to allow for cooling and being directed to a pelletizer or other suitable device to render the extruded ropes into the multiparticulate system. The pelletizer can consist of rollers, fixed knife, rotating cutter and the like. Suitable instruments and systems are available from distributors such as C. W. Brabender Instruments, Inc. of South Hackensack, N.J. Other suitable apparatus will be apparent to those of ordinary skill in the art.

A general pellet manufacturing procedure which may be utilized in accordance with the invention is as follows: Premix the required amount of drug, polymers, and optional binder (wax). Charge a powder feeder with proper amount of drug/excipient blend. Set temperatures of extruder to the required temperature, depending on the formulation. Wait until the corresponding heating zones reach steady temperatures. Start the feeder and the extruder. The drug/excipient powder blend is melted and intimately mixed in the extruder. The diameter of the extruder aperture can be adjusted to vary the thickness of the resulting strand. Set the conveyor belt speed to an appropriate speed (e.g., 3–100 ft/min). Allow the extruded semisolid strand(s) to be congealed and transported to the pelletizer. Additional cooling devices may be needed to ensure proper congealing. (The conveyor belt may not be needed to cool the strand, if the material congeals rapidly enough.). Set the roller speed and cutter speed (e.g., to 3–100 ft/min and 100–800 rpm). Cut the congealed strands to desired size (e.g., 3–5 mm in diameter, 0.3–5 mm in length). Collect the pellet product. Fill a desired weight of pellets into hard gelatin capsules to obtain an appropriate dose of the drug.

Another process for the manufacture of a formulation in accordance with the invention, comprises (a) mechanically working in a high-speed mixer, a mixture of tramadol or a pharmaceutically acceptable salt in particulate form and a particulate, hydrophobic fusible carrier or diluent having a melting point from 35 to 140° C. and optionally a release control component comprising a water soluble fusible material, or a particulate soluble or insoluble organic or inorganic material at a speed and energy input which allows the carrier or diluent to melt or soften, whereby it forms agglomerates; (b) breaking down the larger agglomerates to give controlled release seeds; and (c) continuing mechanically working with optionally a further addition of low percentage of the carrier or diluent. Steps (c) and possible (b) may be repeated one or more times. Stage (a) of the process may be carried out in conventional high speed mixers with a standard stainless steel interior, e.g. a Collette Vactron 75 or equivalent mixer. The mixture is processed until a bed temperature about 40° C. or above is achieved and the resulting mixture acquires a cohesive granular texture, with particle sizes ranging from about 1–3 mm to fine powder in the case of non-aggregated original material. Such material, in the case of the embodiments described below, has the appearance of agglomerates which upon cooling below 40° C. have structural integrity and resistance to crushing between the fingers. At this stage the agglomerates are of an irregular size, shape and appearance. The agglomerates are preferably allowed to cool. The temperature to which it cools is not critical and a temperature in the range room temperature to 37° C. may be conveniently used. The agglomerates are broken down by any suitable means, which will comminute oversize agglomerates and produce a mixture of powder and small particles preferably with a diameter under 2 mm. It is currently preferred to carry out the classification using Jackson Crockatt granulator using a suitable sized mesh, or a Comil with an appropriate sized screen. It has been previously reported that if too small a mesh size is used in the aforementioned apparatus the agglomerates melting under the action of the beater or impeller will clog the mesh and prevent further throughput of mixture, thus reducing yield. A mesh size of 12 has been found adequate. The classified material is returned to the high speed mixer and processing continued. It is believed that this leads to cementation of the finer particles into particles of uniform size range.

In one preferred form of the method of the invention, processing of the classified materials is continued until the hydrophobic fusible materials used begin to soften/melt and optionally additional hydrophobic fusible material is then added. Mixing is continued until the mixture has been transformed into particles of the desired predetermined size range.

In certain processes, it is preferred to supply at least part of the energy input into the ingredients in the high speed mixer by means of microwave energy, in order to ensure uniform energy. Energy may also be delivered through other means such as by a heating jacket or via the mixer impeller and chopper blades. After the particles have been formed they are cooled or allowed to cool, and may then be sieved to remove any over or undersized material.

The resulting particles may be used to prepare dosage units in accordance with the invention in the form of e.g. tablets or capsules in manners know per se.

The formulations of the invention may also be prepared in accordance with procedures set forth in U.S. Pat. No. 3,965,256 (Leslie) which is directed to slow release pharmaceutical compositions comprising a combination of a higher aliphatic alcohol and a hydrated hydroxy-alkyl cellulose. These formulations may be prepared, e.g., by melting and granulating the higher aliphatic alcohol; hydrating the hydroxy alkyl cellulose and granulating the hydrated cellulose compound; blending the active ingredient with either the granulated melt, the granulated alkyl cellulose, or a mixture thereof; and drying the blend of granules. Thereafter, the granules are optionally mixed with an appropriate amount of a pharmaceutically acceptable diluent and compressed into tablets.

The formulations of the invention may also be prepared in accordance with the procedures set forth in U.S. Pat. No. 4,861,598 and 4,970,075 (Oshlack, et al.), wherein the release of therapuetically active agents from controlled release bases is extended by using a combination of a higher aliphatic alcohol and an acrylic resin as the base material. The dosage forms are prepared, e.g., via a wet granulation method wherein most of the excipients (including optional pharmaceutically acceptable diluent when tablets are to be prepared as the ultimate product) with or without the therapeutically active agent are combined together with a granulating fluid until a moist granular mass is obtained; the mass is dried and the resultant granulate sized; the higher aliphatic alcohol is melted and incorporated into the warm granules using a suitable mixer. After cooling, the granules are sized. Optionally, the granules are then lubricated and compressed into tablets.

Stabilization of the Formulations

In order to achieve the curing of the invention, the final formulation is exposed to prolonged elevated temperatures in order to achieve stability. In situations where the hydrophobic material includes only a wax-like substance, the curing is preferably accomplished at a temperature from about 35° C. to about 65° C., for a sufficient time period until stability is achieved. In certain preferred embodiments of the invention, the curing is accomplished at a temperature from about 35° C. to about 65° C., for a time period from about 4 to about 72 hours. In certain preferred embodiments, the curing is conducted at a temperature of from about 40° C. to about 60° C., for a time period from about 5 to about 24 hours. In certain preferred embodiments, the elevated temperature is about 50° C. It is contemplated that the time period needed for curing to an endpoint as described above may actually be longer or shorter than the time period mentioned above. Such curing times which achieve the intended result of a stabilized formulation are considered to be encompassed by the appended claims.

In certain preferred embodiments, the curing is conducted at a temperature of from about 45° C. to about 55° C., for a time period from about 4 to about 72 hours, preferably at least about 24 hours.

The glass transition temperature (Tg) is related to the temperature or temperature range where there is a fundamental change in the physical properties of the polymer. This change does not reflect a change in state, but rather a change in the macromolecular mobility of the polymer. Below the Tg, the polymer chain mobility is severely restricted. Thus, for a given polymer, if its Tg is above room temperature, the polymer will behave as a glass, being hard, non-pliable and rather brittle, properties which could be somewhat restrictive in film coating since the coated dosage form may be subjected to a certain amount of external stress. Additionally, it will be appreciated by those skilled in the art that it may be possible to cure the formulations of the present invention in other manners in order to reach the endpoint at which the coated substrate provides a stable dissolution profile. Such additional curing methods which achieve the intended result of a stabilized formulation are also considered to be encompassed by the appended claims.

The curing endpoint may be determined by comparing the dissolution profile of the cured final formulation immediately after curing (hereinafter referred to as "the initial dissolution profile") to the dissolution profile of the formulation after exposure to accelerated storage conditions or prolonged storage at room temperature. Generally, the curing endpoint may be determined by comparing the dissolution profile of the formulation after exposure to accelerated storage conditions of, e.g., 37° C./80% RH or 40° C./75% RH for a time period of one month to the initial dissolution profile. However, the curing endpoint may be further confirmed by continuing to expose the cured, coated formulation to accelerated storage conditions for a further period of time and comparing the dissolution profile of the formulation after further exposure of, e.g., two months and/or three months, to the initial dissolution profile obtained.

In certain preferred embodiments, the curing endpoint is attained when the data points plotted along a graph of the dissolution Curve obtained after, e.g., exposure to accelerated conditions of 1–3 months, show a release of the active agent (tramadol) which does not vary at any given time point by more than about 20% of the total amount of active agent released when compared to in-vitro dissolution conducted prior to storage. Such a difference in the in-vitro dissolution curves, referred to in the art as a "band range" or a "band width" of, e.g., 20%. In general, where the in-vitro dissolution prior to storage and after exposure to accelerated conditions varies by not more than, e.g., about 20% of the total amount of active agent released, the formulation is considered acceptable when considered by governmental regulatory agencies such as the U.S. FDA for stability concerns and expiration dating. Acceptable band ranges are determined by the FDA on a case-by-case basis, and any band range for a particular pharmaceutical which would be deemed acceptable by such a governmental regulatory agency would be considered to fall within the appended claims. In preferred embodiments, the aforementioned band range is not more than 15% of the total amount of active agent released. In more preferred embodiments, the band range is not more than 10% of the total amount of active agent released.

In general, the length of the studies and the storage test conditions required by regulatory agencies such as the FDA for pharmaceutical formulations are sufficient to cover storage, shipment, and subsequent use. Allowable storage test conditions may vary depending upon the particulars of the product. For example, temperature sensitive drug substances should be stored under an alternative, lower temperature condition, which is then deemed to be the long term testing storage temperature. In such cases, it is generally accepted that the accelerated testing should be carried out at a temperature at least 15° C. above this designated long term storage temperature, together with appropriate relative humidity conditions for that temperature.

A generally accepted accelerated test employed in FDA guidelines relates to the storage of a drug product (e.g., in its container and package) at 80% Relative Humidity (RH) and 37° C. (1985 FDA guidelines). If the product holds up for, e.g., three months under these conditions (chemical stability, dissolution, and physical characteristics), then the drug product will be accorded, e.g., a two year expiration date. This accelerated test is also now also considered to be acceptable if conducted at 75% RH and 40° C. (FDA 1987 guidelines). It has recently been proposed that long-term storage testing be conducted for pharmaceutical formulations at 25° C.±2° C. at not less than 60% RH±5% for a minimum time period of 12 months. It has been further proposed that accelerated testing be conducted for pharmaceutical formulations at 40° C.±2° C. at 75% RH±5% for a minimum time period of 6 months. All of the above-mentioned accelerated testing criteria and others are deemed equivalent for purposes of the present invention, with regard to the determination of stability and the determination of the curing endpoint.

DETAILED DESCRIPTION OF THE PREFERRED EMBODIMENTS

The following examples illustrate various aspects of the present invention. They are not meant to be construed to limit the claims in any manner whatsoever.

EXAMPLE 1

The formulation of Example 1 was prepared via a melt extrusion/granulation technique as follows:

The drug and all the excipients were blended in a proper mixer and the mixture was placed in a powder feeder. The mixture was then fed into a twin screw extruder at elevated temperatures. The twin screw extruder is consisted of a pair of counter rotating screws and a barrel block equipped with heating/cooling zones. The extrudate came out as a thick strand was congealed on a conveyor belt and was broken into smaller pieces. After the excipients were melted and the drug embedded in the molten mixture, the viscous mass was extruded. The extrudate was congealed and hardened while being carried away on a conveyor belt. The extrudate was thereafter granulated using a FitzMill equipped with #1521-0065 screen. The resultant granulates were then mixed with talc and lubricated with magnesium stearate. The lubricated granulates were then compressed into tablets.

The ingredients of Example 1 are set forth in Table 1 below:

TABLE 1

| Ingredients | % | mg/tablet |
|---|---|---|
| tramadol HCl | 44.1 | 200 |
| Ethocel Std 7 | 24.3 | 110 |
| stearyl alcohol | 24.3 | 110 |
| dibutyl citrate | 4.9 | 22 |
| talc | 1.6 | 7.4 |
| magnesium stearate | 0.8 | 3.8 |
| Total: | 100 | 453.2 |

The tablets of Example 1 were tested via the following in-vitro dissolution method. The dissolution test was carried out USP Apparatus II (Paddle Method) at 100 rpm in pH 6.5 phosphate buffer at 37° C. The in-vivo dissolution rate of tramadol HCl from the tramadol tablets of Example 1 was determined by an HPLC method. (This dissolution method was used throughout the Examples). The tramadol tablets of Example 1 provided an in-vitro dissolution indicative of a product suitable for administration on a once-a-day basis.

The dissolution results are set forth in Table 2 below:

TABLE 2

| Time (Hours) | Example 1 % Dissolved |
|---|---|
| 1 | 18 |
| 2 | 24 |
| 4 | 33 |
| 8 | 46 |
| 12 | 57 |
| 18 | 74 |
| 24 | 82 |

The tablets of Example 1 were then film-coated with Opadry® Beige (Y-1-17181-A, from Coloron, Inc.) to a weight gain of 4%. Opadry YS-1-17181-A Beige, includes hydroxypropylmethylcellulose, titanium dioxide, polyethylene glycol 400, synthetic yellow iron oxide, synthetic red iron oxide and polysorbate 80. The inlet temperature of the coating process was set at about 50° C. with an outlet temperature of about 40° C. The spray rate used was about 6–10 g/min with an air volume of about 60 cfm. The tablets were then and stored under 40° C. and 75% relative humidity for two weeks. The following dissolution results show that the drug release rates following the coating and storage are progressively slower. Since the coating material used was a highly water-soluble polymer and the coating level was low (4%), it was surprisingly found that the drug release rate was reduced under the relatively high temperatures used in the coating process (40° C. outlet temperature) and subsequent storage. This was demonstrated via the in-vitro dissolution results set forth in Table 3 below, which sets forth the dissolution data obtained from Example 1 initially after product manufacture (including film-coating), and then dissolution data obtained from Example 1 after two weeks of storage under ambient conditions (i.e., room temperature, ambient humidity):

TABLE 3

| Time (Hours) | Example 1 (FC) % Dissolved | Example 1 (FC, 2W) % Dissolved |
|---|---|---|
| 1 | 13 | 11 |
| 2 | 20 | 16 |
| 4 | 28 | 23 |
| 8 | 39 | 34 |
| 12 | 49 | 43 |
| 18 | 61 | 53 |
| 24 | 70 | 62 |

FC = film-coated; 2W = 2 weeks storage time (after film-coating)

EXAMPLE 2

The tablets of Example 2 were prepared using the same manufacturing process as Example 1. These two batch lots of tablets (Examples 1 and 2) showed similar drug release rates at time zero (dissolution was done right after manufacture, in accordance with the procedures set forth for Example 1). After one month storage under ambient conditions, the tablets showed a slower dissolution rate (dissolution conducted in similar fashion as Example 1). The uncoated tablets were then placed in a 50° C. oven for 1 hour. The following results show that the dissolution rate of the tablet was significantly slower after curing at 50° C. for 1 hour.

TABLE 4

| Time (Hours) | Example 2 (initial) % Dissolved | Example 2 (1 mo old) % Dissolved | Example 2 (1 mo old, 1 hr cure) % Dissolved |
|---|---|---|---|
| 1 | 18 | 16 | 12 |
| 2 | 25 | 23 | 16 |
| 4 | 34 | 32 | 23 |
| 8 | 48 | 45 | 33 |
| 12 | 58 | 56 | 41 |
| 18 | 72 | 69 | 52 |
| 24 | 83 | 79 | 60 |

The results showed that the drug release rate was significantly reduced by exposing to a high temperature, probably due to a tablet curing effect via exposure of the formulation to the near-softening temperature of the polymer.

EXAMPLE 3

In Example 3, tablets were prepared in the same fashion set forth in Example 1. The ingredients of the tablets prepared in Example 3 are set forth in Table 5 below:

TABLE 5

| Ingredients | % | mg/tablet |
|---|---|---|
| tramadol HCl | 55.7 | 200 |
| Ethocel Std 7 | 20.6 | 74 |
| stearyl alcohol | 20.6 | 74 |
| talc | 2.1 | 7.4 |
| magnesium stearate | 1.10 | 3.8 |
| total: | 100 | 359.2 |

Once the tablets of Example 3 were prepared, dissolution testing was conducted according to the procedure set forth in Example 1. The dissolution results are set forth in Table 6 below:

TABLE 6

| Time (Hours) | Example 1 % Dissolved |
|---|---|
| 1 | 24 |
| 2 | 34 |
| 4 | 46 |
| 8 | 62 |
| 12 | 75 |
| 18 | 87 |
| 24 | 95 |

The results indicate that the dissolution rate of the tablets of Example 3 was faster than the targeted dissolution rate provided by Example 1. This was expected, and is due to the reduced amount of excipient used. The tablets of Example 3 were placed in 50° C. oven for 1.5 hrs, 4 hrs, 3 days, 6 days, and 10 days. The dissolution results are listed as follows in Table 7.

TABLE 7

| Time (hrs) | Cured at 50° C. | | | | |
|---|---|---|---|---|---|
| | 1.5 hr | 4 hr | 3 day | 6 day | 10 day |
| 1 | 20 | 18 | 16 | 15 | 16 |
| 2 | 28 | 26 | 23 | 23 | 23 |
| 4 | 38 | 35 | 33 | 32 | 31 |
| 8 | 53 | 49 | 44 | 44 | 43 |
| 12 | 64 | 59 | 54 | 53 | 53 |
| 18 | 76 | 71 | 64 | 64 | 63 |
| 24 | 86 | 81 | 73 | 73 | 71 |

It was observed in the above Examples that the drug release rate slowed down with increased storage time especially if stored under elevated temperatures. By curing the tablets at elevated temperatures (e.g. 50° C.) for, e.g. 4 hours, the drug release rate of tramadol from the hydrophobic material was significantly retarded upon manufacturing and was stable with time under variable storage conditions. The above results indicate that the drug dissolution rate of the cured tablets decreases with increasing curing time and was stable by the time dissolution results were next taken, i.e., after 3 days. Assuming that the dissolution result of the tablets of Example 1 is close to the desired rate, it is apparent that after coating and storage under ambient temperatures, the dissolution progressively slowed down. To prevent this instability in dissolution rate from changing with storage time, a new formulation was prepared with a faster than targeted dissolution (Example 3). The tablets were stored at 50° C. for 1–3 days to promote polymer coalescence in the matrix (curing) and render a targeted dissolution profile.

This example also demonstrates that because curing can slow down the dissolution to a stable endpoint, one can also use curing as a method to aide dissolution retardation, so that less hydrophobic (retarding) excipient can be used. This aspect of the invention is particularly important for relatively high-dose drugs such as tramadol, in that it allows the size of the final unit dose (e.g., tablet) to be reduced relative to an uncured product.

EXAMPLE 4

The lubricated granulation used to prepare Example 3 was used to make Example 4 in larger quantity. The tablets were further film-coated pursuant to the procedure set forth in Example 1 and cured at 50° C. for 1, 2, 3, 6, and 9 days. The dissolution results are shown as set forth in Table 8 below:

TABLE 8

| Time (hrs) | Cured at 50° C. | | | | |
|---|---|---|---|---|---|
| | 1 day | 2 days | 3 days | 6 days | 9 days |
| 1 | 17 | 18 | 17 | 17 | 17 |
| 2 | 23 | 25 | 24 | 24 | 23 |
| 4 | 32 | 34 | 34 | 33 | 32 |
| 8 | 45 | 47 | 47 | 46 | 44 |
| 12 | 55 | 56 | 57 | 55 | 54 |
| 18 | 66 | 68 | 69 | 67 | 65 |
| 24 | 76 | 77 | 78 | 78 | 78 |

The results set forth in Table 8 above demonstrate that curing for a time period of 1 day at 50° C. is sufficient to cure the tablets to a stable endpoint (at which the release rate of the drug from the formulation is unchanged after further exposure to accelerated storage conditions). A curing period of up to 9 days does not significantly change the dissolution profile of tramadol from the cured tablets.

The tablets which were cured at 50° C. for 3 days were put on stability tests under 25° C./60% RH and 40° C./75% RH for 1 and 3 months. The dissolution results are shown as follows in Table 9:

TABLE 9

| Time (hrs) | 25° C./60% RH | | | 45° C./75% RH | |
| --- | --- | --- | --- | --- | --- |
| | initial | 1 mo | 3 mo | 1 mo | 3 mo |
| 1 | 17 | 18 | 18 | 16 | 16 |
| 2 | 24 | 26 | 25 | 23 | 23 |
| 4 | 36 | 36 | 34 | 33 | 32 |
| 8 | 47 | 49 | 47 | 47 | 45 |
| 12 | 57 | 60 | 57 | 57 | 55 |
| 18 | 69 | 72 | 68 | 69 | 66 |
| 24 | 78 | 81 | 74 | 79 | 72 |

Compared to the initial dissolution data, the stability results indicated that the tablets, once cured, have stable dissolution release characteristics over various storage conditions and periods.

EXAMPLE 5

In Example 5, a different formulation was made containing a similar wax (cetostearyl alcohol) to that used in the above Examples, and polymer. The formulation was prepared according to an alternative method as set forth in the specification. The tablets of Example 5 include the ingredients and amounts set forth in Table 10 below to make the controlled release tablets:

TABLE 10

| Ingredients | % | mg/tablet |
| --- | --- | --- |
| tramadol HCl | 43.5 | 100 |
| lactose | 30.0 | 68 |
| cetostearyl alcohol | 18.2 | 42 |
| Surelease ™ (solid) | 6.5 | 15 |
| talc | 1.3 | 3 |
| magnesium stearate | 0.9 | 2 |
| Total: | 100 | 230 |

Surelease is an aqueous dispersion of ethylcellulose containing Dibutyl Sebacate as the plasticizer.

The formulation was prepared by spraying the Surelease dispersion onto a tramadol HCl/lactose mixture in a fluid bed dryer; mixing molten cetostearyl alcohol into the granulates in a high shear mixer; passing the mixture through a screen and mixing with talc; lubricating the resultant material with magnesium stearate; and compressing the lubricated granulates into tablets.

Dissolution testing (performed in accordance with Example 1) provided the following results set forth in Table 11:

TABLE 11

| Time (Hours) | Initial % Dissolved | Stored 3 mo at 30° C./60% RH % Dissolved | Stored 3 mo at 45° C./75% RH % Dissolved |
| --- | --- | --- | --- |
| 1 | 43 | 38 | 33 |
| 2 | 56 | 50 | 43 |
| 4 | 71 | 64 | 54 |
| 8 | 87 | 79 | 68 |
| 16 | 97 | 91 | 82 |

From the results set forth in Table 11, it can be seen that the tramadol release rate of this tablet formulation which was manufactured with different excipients and a different method of manufacture (as compared to Examples 1–4) also slowed down after storage under high temperatures. Therefore, the formulations can be stabilized by subjecting the final product to a curing step, as set forth above.

EXAMPLE 6

In Example 6, a further different formulation was made containing a different waxy material (hydrogenated vegetable oil) as compared to that used in the above Examples. No hydrophobic polymer was included as part of the hydrophobic material. The formulation was prepared according to an alternative method as set forth in the specification. The tablets of Example 6 include the ingredients and amounts set forth in Table 12 below to make the controlled release tablets:

TABLE 12

| Ingredients | % | mg/tablet |
| --- | --- | --- |
| tramadol HCl | 52.3 | 300 |
| hydrogenated vegetable oil | 42.7 | 245 |
| talc | 3.0 | 17.2 |
| magnesium stearate | 2.0 | 11.5 |
| total: | 100 | 573.7 |

The tablets were prepared as follows. The tramadol HCl and hydrogenated oil were placed in a jacketed bowl and mixed until melting and granulation occured. The granulated material was then transfered to a metal tray, and cooled to 42° C. An appropriate grinder was then used to mill the granulated material. The milled material was then returned to the jacketed bowl, and mixed until melt pelletization occured. The resultant pelletized material is screened through a 2 mm then 0.5 mm screen, and the fraction of 0.5–2 mm particles (granulates) were retained. The granulates were then mixed with talc and lubricated with magnesium stearate, and the resultant lubricated granulates were compressed into tablets.

The tablets of Example 6 were then subjected to dissolution testing in accordance with the procedures set forth in Example 1. The results are set forth in Table 13 below:

TABLE 13

| Time (Hours) | Example 6 % Dissolved | Example 6 stored at 50° C. 3 days % Dissolved |
| --- | --- | --- |
| 1 | 20 | 18 |
| 2 | 27 | 25 |
| 4 | 37 | 33 |
| 8 | 50 | 45 |
| 12 | 61 | 54 |
| 18 | 74 | 65 |
| 24 | 82 | 74 |

*Tablet Hardness = 5 kp

The formulation of Example 6 provides an in-vitro drug release profile indicative of a final product which may be administered on a once-a-day basis. However, after storage at 50° C. for 3 days, the drug dissolution rate of the tablets of Example 6 slowed down.

EXAMPLE 7

Because Example 4 was prepared in a small scale (less than 1 kg batch size), in Example 7 a scale-up lot was prepared in a similar manner with a larger extruder. In Example 7, however, the tablets were cured at 50° C. for 24 hours prior to coating. After the curing step was completed, the tablets were film-coated using a coating pan (AccelaCota 48" pan) to a weight gain of 4% using Opadry Beige under the following conditions: inlet temperature: 50–56° C.; Outlet temperature: 38–40° C.; spray rate=about 200 ml/min; Air flow: 2100–2400 cfm; Atomization air pressure: 65 psi.

The dissolution data of newly prepared cured tablets (initial or "time zero") and tablets stored under room conditions (25° C./60% RH) and accelerated storage ("stress") conditions (40° C./75% RH) were obtained in accordance with the procedures set forth in Example 1. The results are provided in Table 14 below:

TABLE 14

| Time | 25° C./60% RH | | | 40° C./75% RH | | |
|---|---|---|---|---|---|---|
| (hrs) | initial | 3 mo | 6 mo | 1 mo | 3 mo | 6 mo |
| 1 | 24 | 22 | 23 | 21 | 21 | 22 |
| 2 | 33 | 31 | 31 | 31 | 31 | 31 |
| 4 | 45 | 42 | 43 | 42 | 43 | 43 |
| 8 | 61 | 57 | 58 | 57 | 58 | 59 |
| 12 | 72 | 66 | 68 | 68 | 69 | 70 |
| 18 | 83 | 77 | 80 | 79 | 81 | 80 |
| 24 | 92 | 84 | 88 | 89 | 88 | 89 |

The results show that the dissolution rate of cured tablets is stable after storage under various conditions. Therefore, the formulations can be stabilized by subjecting the final product to a curing step, as set forth above. It is noted that these tablets were cured before coating. The tablets in previous examples were coated before curing. The results demonstrate that conducting the curing before or after the coating procedure does not make a difference.

To assess the steady-state bioavailability of the formulation of Example 7, a multidose, three-way crossover study was conducted on 24 normal volunteers. These subjects received 50 mg Ultram™ (immediate release Tramadol tablets commercially available from Johnson & Johnson) every six hours, or once a day. Venous blood samples were taken over 24 hours at predetermined time points on the 5th day. FIG. 1 depicts the mean plasma tramadol concentrations (ng/ml) over 24 hours on the 5th day after multiple doses.

Table 15 summarizes tramadol pharmacokinetic parameters (arithmetic means) of the 5th day after multiple doses of Ultram and Example 7.

TABLE 15

| Pharmacokinetic Parameters | Ultram | Example 7 | Example 7/ Ultram (%) |
|---|---|---|---|
| AUC (0-Last) | 1694 | 1648 | 105 |
| Cmax (ng/ml) | 109 | 97 | 103 |
| Cmin (ng/ml) | 45 | 40 | 89 |
| % fluctuation | 184 | 146 | 77 |
| Tmax (hrs) | 2.0 | 8.3 | 272 |
| Trough (ng/ml) | 67 | 42 | 69 |

EXAMPLE 8

Previous examples demonstrated that tramadol sustained release formulations containing stearyl alcohol and ethylcellulose (hydrophobic polymer) demonstrated a curing effect (dissolution retardation) after exposing to 50° C. temperature for 24 hours.

In Example 8, a tramadol sustained release formulation containing stearyl alcohol and no hydrophobic polymer was prepared in order to determine whether this curing effect existed if only stearyl alcohol is used.

The tablets of Example 8 were prepared as follows. First, stearyl alcohol was placed in a stainless steel beaker and melted on a hot plate. Tramadol HCl was placed in a Hobart Mixer. The molten stearyl alcohol was poured into the tramadol HCl powder while the mixer blade was turning. The mixture was allowed to congeal and cool to room temperature. The mixture was milled and talc and magnesium stearate were added. The lubricated granulation was compressed into tablets of 5–6 kP. The tablets were cured in a 50° C. oven for 24 hours. The ingredients/amounts for the tablets of Example 8 are set forth in Table 16:

TABLE 16

| Ingredients | % | mg/tablet |
|---|---|---|
| tramadol HCl | 55.7 | 200 |
| stearyl alcohol | 41.1 | 148 |
| talc | 2.1 | 7.4 |
| magnesium stearate | 1.10 | 3.8 |
| Total: | 100 | 359.2 |

The tablets of Example 8 were then subjected to dissolution testing in accordance with the procedures set forth in Example 1, both prior to curing and after curing at 50° C. for 24 hours. The results are set forth in Table 17 below:

TABLE 17

| Time (Hours) | Example 8 (prior to curing) % Dissolved | Example 8 (after curing at 50° C. for 24 hours) % Dissolved |
|---|---|---|
| 1 | 43 | 39 |
| 2 | 61 | 55 |
| 4 | 83 | 79 |
| 8 | 99 | 99 |
| 12 | 102 | 102 |
| 18 | 103 | 102 |
| 24 | 104 | 103 |

A curing effect was observed after the tablets were cured. However, the extent of dissolution retardation was not as significant as compared to previous examples. While the invention has been illustrated with respect to particular formulations wherein a tramadol sustained release formulation is prepared which includes a wax or wax-like material which has been softened or melted during manufacture of the dosage form, it will be appreciated by those skilled in the art of pharmaceutical formulation that many other processes for preparing matrix formulations in which the wax or wax-like material (or a material which acts like the wax or wax-like material in the exemplified formulations) has been softened, melted, or heated to a temperature above its glass transition temperature would be useful in the preparation of formulations in accordance with the invention. Furthermore, it will be appreciated by persons skilled in the art of pharmaceutical formulations that the time and temperature necessary to reach a curing endpoint as defined herein can be varied depending upon the particular ingredients and amounts thereof contained in any particular formulation. Further, in certain situations it may be possible to increase the curing temperature and decrease curing time, and vice-versa. Such obvious modifications can be made without departing from the spirit or scope of the invention, and are deemed to be within the scope and equivalence of the appended claims.

What is claimed is:

1. A stabilized sustained release oral solid dosage form containing tramadol as the active agent, comprising an effective amount of tramadol or a pharmaceutically acceptable salt thereof dispersed in a matrix of a hydrophobic material comprising a substance which was melted or softened during the preparation of said matrix, said solid dosage form being cured at a temperature from about 35° C. to about 65° C. for a sufficient time such that an endpoint is reached at which said solid dosage form provides a stable dissolution profile, said endpoint being determined by comparing the dissolution profile of said solid dosage form immediately after curing to the dissolution profile of said solid dosage form after exposure to accelerated storage conditions of at least one month at 40° C. and 75% relative humidity.

2. The stabilized sustained release oral solid dosage form of claim 1, wherein the curing is conducted at a temperature from about 40° C. to about 60° C. for a time period from about 4 to about 72 hours.

3. The stabilized sustained release oral solid dosage form of claim 1, wherein the curing is conducted at a temperature from about 45° C. to about 55° C. for a time period from about 4 to about 72 hours.

4. The stabilized sustained release oral solid dosage form of claim 1, wherein the curing is conducted for a time period of about 24 hours.

5. The stabilized sustained release oral solid dosage form of claim 1, wherein said substance is hydrogenated castor oil.

6. The stabilized sustained release oral solid dosage form of claim 1, wherein said hydrophobic material further comprises a hydrophobic polymer selected from the group consisting of acrylic polymers, alkylcelluloses and mixtures thereof.

7. The stabilized sustained release oral solid dosage form of claim 1, further comprising a hydrophilic polymer.

8. The stabilized sustained release oral solid dosage form of claim 7, wherein said hydrophilic polymer is a cellulose ether.

9. The stabilized sustained release oral solid dosage form of claim 1, wherein said matrix comprises tramadol, a higher aliphatic alcohol, and a hydrophobic polymer selected from the group consisting of acrylic polymers, alkylcelluloses and mixtures thereof.

10. The stabilized sustained release oral solid dosage form of claim 1, wherein said substance is hydrogenated vegetable oil.

11. The stabilized sustained release oral solid dosage of claim 1, which is a tablet.

12. The stabilized sustained release oral solid dosage form of claim 1, which releases an amount of tramadol which does not vary at any given dissolution time point by more than about 20% of the total amount of tramadol released at that dissolution time point, when compared to in-vitro dissolution conducted prior to said accelerated storage conditions.

13. The stabilized sustained release oral solid dosage form of 6, wherein said hydrophobic polymer comprises from about 0% to about 80% by weight, of the hydrophobic material.

14. The stabilized sustained release oral solid dosage form of 6, wherein said hydrophobic polymer comprises from about 30% to about 50% by weight, of the hydrophobic material.

15. A process for preparing a stabilized sustained release oral solid dosage form containing tramadol as the active agent, comprising preparing a matrix comprising tramadol or a pharmaceutically acceptable salt thereof dispersed in a matrix of a hydrophobic material comprising a substance which is melted or softened during the preparation of said matrix; and thereafter curing said matrix at a temperature from about 35° C. to about 65° C. for a sufficient time such that an endpoint is reached at which said matrix provides a stable dissolution profile, said endpoint being determined by comparing the dissolution profile of said matrix immediately after curing to the dissolution profile of said matrix after exposure to accelerated storage conditions of at least one month at 40° C. and 75% relative humidity.

16. The process of claim 15, further comprising compressing said matrix into a tablet prior to said curing step.

17. The process of claim 16, wherein said tablets are prepared by feeding said tramadol and said hydrophobic material, together with further optional pharmaceutical excipients, into an extruder at elevated temperatures sufficient to soften or melt said substance;

extruding the mixture;

granulating the mixture;

lubricating the granulate; and then compressing the granulate into tablets.

18. The process of claim 16, wherein said tablets are prepared by spraying a hydrophobic polymer dispersion onto a mixture of tramadol and an inert diluent in a fluid bed dryer to obtain granulates;

mixing said substance in a molten state into the granulates in a high shear mixer;

passing the mixture through a screen and mixing with talc;

lubricating the resultant material; and, compressing the lubricated granulates into tablets.

19. The process of claim 16, wherein said tablets are prepared by pouring said substance in a molten state onto the tramadol in a pharmaceutically suitable mixer;

allowing the mixture to congeal and cool; and thereafter milling the mixture;

lubricating the mixture; and compressing lubricated granulation into tablets.

20. The process of claim 16, wherein said tablets are prepared by by melting and granulating said substance;

hydrating a cellulose ether and granulating the same;

blending the tramadol with either the granulated melt, the granulated cellulose ether, or a mixture thereof;

drying the granules; and thereafter optionally mixing with an appropriate amount of a inert pharmaceutically acceptable diluent and compressing the mixture tablets.

21. The process of claim 16, wherein said hydrophobic material comprises a hydrophilic or hydrophobic polymer in addition to said substance, and said tablets are prepared by (a) wet granulating said hydrophobic or hydrophilic polymer and optional diluents with or without said tramadol;

(b) drying and sizing the resultant granulate;

(c) combining said tramadol with the granulate if not previously accomplished in step (a);

incorporating said substance in a molten state into said granules using a suitable mixer;

(d) cooling and sizing the granules; and thereafter (e) lubricating the granules compressing the lubricated granules into tablets.

22. The process of claim 15, wherein the curing is conducted at a temperature from about 40° C. to about 60° C. for a time period from about 4 to about 72 hours.

23. The process of claim 15, wherein the curing is conducted at a temperature from about 45° C. to about 55° C. for a time period from about 4 to about 72 hours.

24. The process of claim 15, wherein the curing is conducted for a time period of about 24 hours.

25. The stabilized sustained release oral solid dosage form of claim 1, wherein the in-vitro dissolution rate of the dosage form after curing when measured by the USP Apparatus 2 (Paddle Method) at 100 rpm in pH 6.5 phosphate buffer at 37° C. is from about 20 to about 50% tramadol released after about 1 hour;

from about 40 to about 75% tramadol released after about 2 hours;

from about 60 to about 95% tramadol released after about 4 hours;

from about 80 to about 100% tramadol released after about 8 hours; and from about 90 to about 100% tramadol released after about 12 hours.

26. The stabilized sustained release oral dosage form of claim 25, wherein the dosage form provides a $T_{max}$ at about 1.5 to about 8 hours after administration of the dosage form to a human patient.

27. The stabilized sustained release oral dosage form of claim 25, wherein the dosage form provides a $T_{max}$ at about 2 to about 7 hours after administration to a human patient.

28. The stabilized sustained release oral dosage form of claim 25, which provides a $W_{50}$ (width of the plasma profile a 50% $C_{max}$) in from about 7 to about 16 hours.

29. The stabilized sustained release oral solid dosage form of claim 1, wherein the in-vitro dissolution rate of the dosage form after curing when measured by the USP Apparatus 2 (Paddle Method) at 100 rpm in pH 6.5 phosphate buffer at 37° C. is from about 0 to about 50% tramadol released after about 1 hour;

from about 0 to about 75% tramadol released after about 2 hours;

from about 10 to about 95% tramadol released after about 4 hours;

from about 35 to about 100% tramadol released after about 8 hours;

from about 55 to about 100% tramadol released after about 12 hours;

from about 70 to about 100% tramadol released after about 16 hours; and more than about 90% tramadol released after about 24 hours.

30. The stabilized sustained release oral solid dosage form of claim 29, wherein the dosage form provides a $T_{max}$ at about 3 to about 6 hours after administration to a human patient.

31. The stabilized sustained release oral solid dosage form of claim 29, wherein the dosage form provides a $T_{max}$ at about 4 to about 5 hours after administration to a human patient.

32. The stabilized sustained release oral dosage form of claim 29, which provides a $W_{50}$ (width of the plasma profile a 50% $C_{max}$) from about 10 to about 33 hours.

33. The stabilized sustained release oral solid dosage form of claim 1, wherein the in-vitro dissolution rate of the dosage form after curing when measured by the USP Apparatus 2 (Paddle Method) at 100 rpm in pH 6.5 phosphate buffer at 37° C. is from about 0 to about 30% tramadol released after about 1 hour;

from about 0 to about 40% tramadol released after 2 hours; from about 3 to about 55% tramadol released after about 4 hours;

from about 10 to about 65% tramadol released after about 8 hours;

from about 20 to about 75% tramadol released after about 12 hours;

from about 30 to about 88% tramadol released after about 16 hours;

from about 50 to about 100% tramadol released after about 24 hours; and more than about 80% tramadol released after about 36 hours.

34. The stabilized sustained release oral solid dosage form of claim 1, wherein the in-vitro dissolution rate of the dosage form after curing when measured by the USP Apparatus 2 (Paddle Method) at 100 rpm in pH 6.5 phosphate buffer at 37° C. is from about 15 to about 25% tramadol released after about 1 hour;

from about 25 to about 35% tramadol released after about 2 hours;

from about 30 to about 45% tramadol released after about 4 hours;

from about 40 to about 60% tramadol released after about 8 hours;

from about 55 to about 70% tramadol released after about 12 hours; and from about 60 to about 75% tramadol released after about 16 hours.

35. The stabilized sustained release oral solid dosage form of claim 1, wherein the in-vitro dissolution rate of the dosage form after curing when measured by the USP Apparatus 2 (Paddle Method) at 100 rpm in pH 6.5 phosphate buffer at 37° C. is from about 5 to about 50% tramadol released after about 1 hour, between about 10 and about 75% tramadol released after about 2 hours, between about 20 and about 95% tramadol released after about 4 hours, between about 40 and about 100% tramadol released after about 8 hours, more than about 50% tramadol released after about 12 hours, more than about 70% tramadol released after about 18 hours and more than about 80% (by weight) tramadol released after about 24 hours.

36. The stabilized sustained release oral solid dosage form of claim 1, wherein said substance is paraffin.

37. The stabilized sustained release oral solid dosage form of claim 1, wherein said substance is a higher aliphatic alcohol.

38. The stabilized sustained release oral solid dosage form of claim 1, wherein said substance is a long chain fatty acid.

39. The stabilized sustained release oral solid dosage form of claim 1, wherein said substance is a fatty acid ester.

40. The stabilized sustained release oral solid dosage form of claim 1, wherein said substance is a natural wax.

41. The stabilized sustained release oral solid dosage form of claim 1, wherein said substance is a synthetic wax.

42. The stabilized sustained release oral solid dosage form of claim 1, wherein said substance is a natural oil.

43. The stabilized sustained release oral solid dosage form of claim 1, wherein said substance is a synthetic oil.

* * * * *